United States Patent [19]

Nguyen et al.

[11] Patent Number: 5,272,909
[45] Date of Patent: Dec. 28, 1993

[54] METHOD AND DEVICE FOR TESTING VENOUS VALVES

[75] Inventors: Than Nguyen; Aws Nashef, both of Huntington Beach; Amir H. Abolfathi, Laguna Hills; David W. Wieting; Denis Lee, both of Irvine, all of Calif.

[73] Assignee: Baxter International Inc., Deerfield, Ill.

[21] Appl. No.: 691,258

[22] Filed: Apr. 25, 1991

[51] Int. Cl.$^5$ .......................... A61F 2/24; A61B 5/00; G01M 19/00
[52] U.S. Cl. ...................................... 73/37; 73/168; 73/866.4; 128/668
[58] Field of Search .................... 73/168, 866.4, 865.9, 73/37, 4 R, 3; 128/668

[56] References Cited

U.S. PATENT DOCUMENTS

| | | | |
|---|---|---|---|
| 4,381,663 | 5/1983 | Swanson | 73/37 |
| 4,450,710 | 5/1984 | Nettekoven | 73/37 |
| 4,546,642 | 10/1985 | Swanson | 73/37 |
| 4,598,579 | 7/1986 | Cummings et al. | 73/37 |
| 4,638,811 | 1/1987 | Bisera et al. | 128/673 |
| 4,682,491 | 7/1987 | Pickard | 73/37 |
| 4,893,494 | 1/1990 | Hort | 73/37 X |
| 5,176,153 | 1/1993 | Eberhardt | 73/37 X |

FOREIGN PATENT DOCUMENTS 0320441 6/1989 European Pat. Off. .

OTHER PUBLICATIONS

Lee, et al. "In Vitro Testing of Venous Valves", Trans Am Soc Artif Intern Organs 1991, vol. 37, Sep. 1991, p. 266 & p. 268 (p. 267 missing).
Hanle, et al. "In vitro velocity measurements down stream from the Ionescu-Shiley aortic bioprosthesis in steady and pulsatile flow", Medical & Biological Engineering & Computing, Sep. 1986 pp. 449, 452-459, (pp. 450-451 missing).
Laxminarayan, et al. "A pulse duplicator model for testing of heart valves", edited by Kondraske, G. and Robinson, C., IEEE/Engineering in Medicine and Biology Society, 8th Annual Conf., Nov. 1986 pp. 120-123.
Wieting, David W., "Dynamic Flow Characteristics of Heart Valves" (Dissert. to faculty of UT Austin, May 1969) pp. 36-43.
Vivitro Systems, Inc. Brochure "Function Testing with Reference to USA (FDA) Guidelines" pp. 1-4 & A1-A12 Jun. 1987.
Vivitro Systems, Inc. Brochure "In Vivo & In Vitro Services and Instrumentation" (2 pages) by Jun. 1991 & 7 page brochure same title Feb. 1987.
Vivitro Systems, Inc. Brochure, "SUPERDUP'R SD 6891 Model Left Heart and Systemic Load"; (2 pages) pub. by Jun. 1991.
McCaughan, John J. Jr. et al., "In Vitro Observations of Greater Saphenous Vein Valves During Pulsatile and Nonpulsatile Flow and Following Lysis", Journal of Vascular Surgery 1:356-361 (1984).
Ku, David N. et al., "The Contribution of Valves to Saphenous Vein Graft Resistance", Journal of Vascular Surgery, 6:274-279 (1987).
Walsh, Daniel B. et al., "Valvular Obstruction of Blood Flow through Saphenous Veins", Journal of Surgical Research, 42:39-42 (1987).
Taheri, S. A. et al., "Experimental Prosthetic Vein Valve", American Journal of Surgery, 156:111-114 Aug. 1988.

*Primary Examiner*—Tom Noland
*Attorney, Agent, or Firm*—Robert Buyan; Debra D. Condino

[57] ABSTRACT

A method and device for testing artificial or natural venous valves. The device comprises (a) a fixture for mounting a sample valve on a liquid flow path, (b) a muscle pump component and/or (o) respiratory pump component and/or (d) capacitance reservoir component and/or (e) vertical hydrostatic column component, all of the components being fluidly connected to the flow path to mimic the muscle pump, respiratory pump, capacitance and hydrostatic impedance effects of actual in situ venous circulation in the mammalian body. The invention includes methods of testing venous valves by mimicking known hemodynamic flow conditions within a mammalian body.

20 Claims, 7 Drawing Sheets

METHOD AND DEVICE FOR TESTING VENOUS VALVES

FIELD OF THE INVENTION

The present invention pertains generally to physiological laboratory equipment and more particularly to a device for testing artificial or natural venous valves for safety and efficacy, under conditions which are simulative of the natural hemodynamic conditions encountered by venous valves in situ.

BACKGROUND OF THE INVENTION

In mammals, the hemodynamics of venous return (i.e. bloodflow through the veins of the body) are influenced by three significant factors, including: (1) the action of the heart itself in continually pumping blood through the arterial circulation and into the capillary beds of the vascular tree; (2) a "muscle pump" effect created by movements of the visceral organs and somatic muscles; and (3) a "respiratory pump" effect created by the normal cyclic variations in intrathoracic pressure which occur during respiration due to respiratory movement of the thoracic muscles and diaphragm.

In many mammals, small semilunar valves known as "venous valves" (syn. valvulae vienosa) are found within the extremity veins. Such venous valves function as oneway check valves to maintain the flow of venous return blood in the direction toward the heart, while preventing blood from backflowing in a direction away from the heart. Such venous valves are particularly important in the veins of the lower extremities, as venous blood returning from the lower extremities is required to move against a long hydrostatic column, especially when the subject animal is in a standing or upright position.

Acquired venous valvular incompetence occurs in humans as a result of trauma (e.g. crushing injury to the vein) or disease (e.g. inflammatory thrombophlebitis). Hereditary factors may also result in incompetence or absence of venous valves in some individuals.

Any condition which results in chronic incompetence or absence of venous valves, especially in the veins of the lower extremities, is likely to give rise to troublesome pathologic consequences. For example, incompetence or absence of venous valves at the saphenofemoral or saphenopopliteal junction may result in varices of the primary (and/or secondary) veins of the lower leg and ankle. Such veins tend to become enlarged, dilated and tortuous, often resulting in pain as well as noncosmetic appearance. Additionally, incompetence or absence of venous valves may cause deep venous hypertension of the lower limbs with resultant lymphedema, aberrant pigmentation of the skin and, in severe cases, the formation of necrotizing lesions (i.e. "venous ulcers"). If not successfully treated, the presence of necrotizing lesions may eventually require limb amputation.

Several surgical procedures have been developed for treating venous valvular insufficiency. Such surgical procedures include: (a) surgical valvuloplasty procedures wherein some or all of the incompetent valves are surgically repaired or reconstructed; see, Garcia-Rinaldi, R, et al., "Femoral Vein Valve Incompetence: Treatment with a Xenograft Monocusp Patch", Journal of Vascular Surgery, Vol 3, No. 6; pp. 932-935 (June 1986); (b) surgical bypass procedures wherein a segment of viable vein is utilized to bypass a region of veins having incompetent or absent venous valves positioned therein; and (c) surgical valve transplantation procedures whereby incompetent or absent venous valves are excised, removed and replaced by transplanted segments of viable vein having functioning venous valves therein. See, Gotlob R. and May R. Venous Valves V Section 3, pp. 183-208, "Reconstruction of Venous Valves" (Springer-Verlang/Wien 1986). Additionally, efforts have been directed toward the development of manmade prosthetic venous valves for surgical implantation in patients who suffer from venous valvular incompetence. See, Hill. R. et al., "Development of a Prosthetic Venous Valve"; Journal of Biomedical Materials Research, Vol. 19, pp. 827-832 (1985); Taheri. S. A. et al., "Experimental Prosthetic Vein Valve", The American Journal of Surgery, Vol. 156, pp. 111-114 (1988).

Although surgical venous valve "bypass" and "transplant" procedures may be viable modes of treating chronic venous valvular insufficiency, the process of locating and harvesting autograft tissue (i.e. segments of viable vein taken from the patient's own veins and used for subsequent transplant or bypass graft) are often problematic (a) because of difficulties encountered in locating suitable segments of vein having viable venous valves therein and/or (b) because of the necessity for performing a separate incision or second surgery to harvest, a venous valve autograft from a separate location and/or (c) size mismatching of the harvested venous valve autograft relative to the implant site, as may result in subsequent failure of the implanted valve.

In view of the limitations and shortcomings in the prior art uses of autograft tissue for venous valvular transplantation or bypass grafting, it is desirable to develop methods of preparing and preserving venous valvular allograft or heterograft tissues harvested from the veins of animals or cadaverous human sources for subsequent surgical implantation (i.e. valvular transplantation or bypass grafting) in humans suffering from venous valvular insufficiency. Also, it is desirable to design and develop implantable artificial venous valves (i.e. made of synthetic materials) capable of carrying out the same physiological functions as venous valves of natural origin.

In furtherance of programs aimed at developing means and methods of preparing venous valvular implants of biological or artificial origin, there exists a need for a mechanical device capable of testing the function of such natural or artificial venous valves. Such venous valve testing device will preferably be capable of mimicking or simulating the normal physiological and hemodynamic conditions encountered by venous valves in situ. The development of such venous valve function testing device will provide a means for conveniently testing new methods and materials for preparing artificial and/or natural venous valves for subsequent surgical implantation and will minimize the need for conducting such testing and experimentation in live animals.

While the prior art has included several devices for functional testing of heart valves (e.g. mitral valves, aortic valves). Such heart valve function testing devices are not suitable for use in testing the function of venous valves because the hemodynamic variables encountered by venous valves in situ are grossly different from those encountered by heart valves. One example of a commercially available heart valve function testing device of the prior art is known as the "Heart and Load" Model MHL 6991, (Vivitro Systems, Inc., Victoria, British Columbia).

It is noted that, in the prior art, there has also existed at least one durability/fatigue testing device for testing the long term e.g. 5 months) operability of venous valves. However, such durability/fatigue testing device serves only to effect continual oscillatory flow of liquid through the subject valve and does not incorporate means for altering and changing hemodynamic pressure and flow variables (i.e. "respiratory pump" effects, capacitance changes, etc.) to permit simulation of various hemodynamic pressure and/or flow waveforms as may be encountered by venous valves in situ. One example of a venous valve durability/fatigue testing device is disclosed in Taheri, S. A. et al., "Experimental Prosthetic Vein Valve", American Journal of Surgery, Vol. 156, pp. 111-114 (1988).

Given the foregoing shortcomings of the prior art, there exists a need for a mechanical venous valve function testing device which is capable of mimicking or simulating various hemodynamic and flow conditions encountered by venous valves in situ.

SUMMARY OF THE INVENTION

The present invention overcomes some or all of the shortcomings of the prior art by providing a method and device for testing the function of biological or artificial venous valves.

In accordance with the invention there is provided a mechanical device for creating hemodynamic flow and pressure conditions which are simulative of the actual flow and pressure conditions encountered by venous valves, in situ.

In accordance with the invention, there is provided a venous valve testing device which comprises:

(a) a sample mounting chamber for holding an artificial or natural venous valve in a relatively fixed position and having a fluid flow conduit extending therethrough such that a liquid (e.g. 0.9% NACL solution) may flow through such sample valve;

(b) a muscle pump fluidly connected to the sample chamber flow conduit to effect a muscle pump effect on fluid flowing through the sample valve;

(c) a respiratory pump fluidly connected to the sample chamber flow conduit to effect a respiratory pump effect on liquid flowing through the sample valve; and (d) a capacitance resevoir to effect a variable capacitance effect on liquid passing through the sample valve.

Further in accordance with the invention, the venous valve testing device may further comprise a hydrostatic impedence column or vertical liquid filled tube fluidly connected to the sample chamber flow conduit to provide a hydrostatic fluid effect against which liquid passing through the sample valve must flow.

Further in accordance with the invention, the individual components of the venous valve testing device may be fluidly interconnected to form a common recirculation loop whereby liquid may be continually recirculated through the device.

Further in accordance with the invention, the device may incorporate a temperature control apparatus or system for controlling and maintaining the temperature of liquid being circulated through the device.

Further in accordance with the invention, various attendant monitoring and measuring apparatus may be attached to the device for monitoring and measuring variables such as temperature, flow rate and pressure of liquid passing through the device.

Further in accordance with the invention, there is provided a method of testing the function of artificial or biological venous valves by mechanically creating and maintaining a flow of liquid through such natural or artificial venous valve in a manner which is a reproduction or simulation of the actual hemodynamic flow conditions encountered by a venous valve at a specific site in the venous vasculature of an animal having known physiological variables (e.g. heart rate, respiration rate/depth) as well as known exercise and/or postural conditions.

Further in accordance with the invention, there is provided a method and device for testing artificial or biological venous valves by creating and maintaining desired liquid flow conditions through such artificial or biological venous valve through the use of a) a muscle pump and/or b) a respiratory pump and/or a capacitance reservoir and/or d) a hydrostatic fluid column which, alone or in combination, will provide a previously known or specifically desired flow waveform through such artificial or natural venous valve.

Further objects and advantages of the invention will become apparent upon reading and understanding of the following detailed description, the accompanying drawings, and the specific examples set forth therein.

DETAILED DESCRIPTION OF THE PREFERRED EMBODIMENT

The following detailed description and the accompanying drawings are provided for purposes of describing and illustrating a specific embodiment of the invention and are not intended to limit the scope of the invention in any way.

i. General Structure and Operation of the Venous Valve Function Tester

Figure 1:
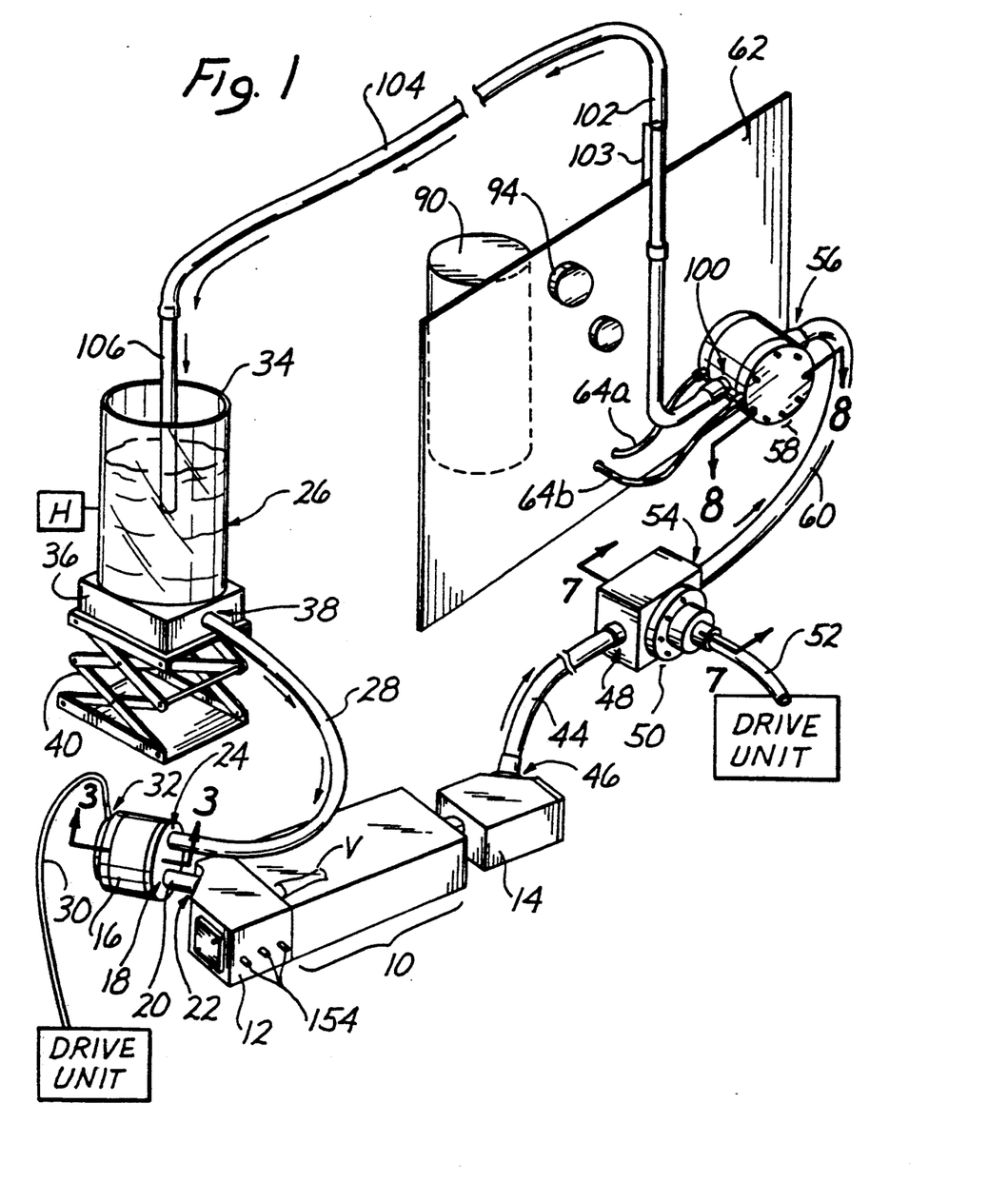
FIG. 1 is a front perspective view of one embodiment of a venous valve testing device of the present invention.
Figures 1A, 2, 2A:
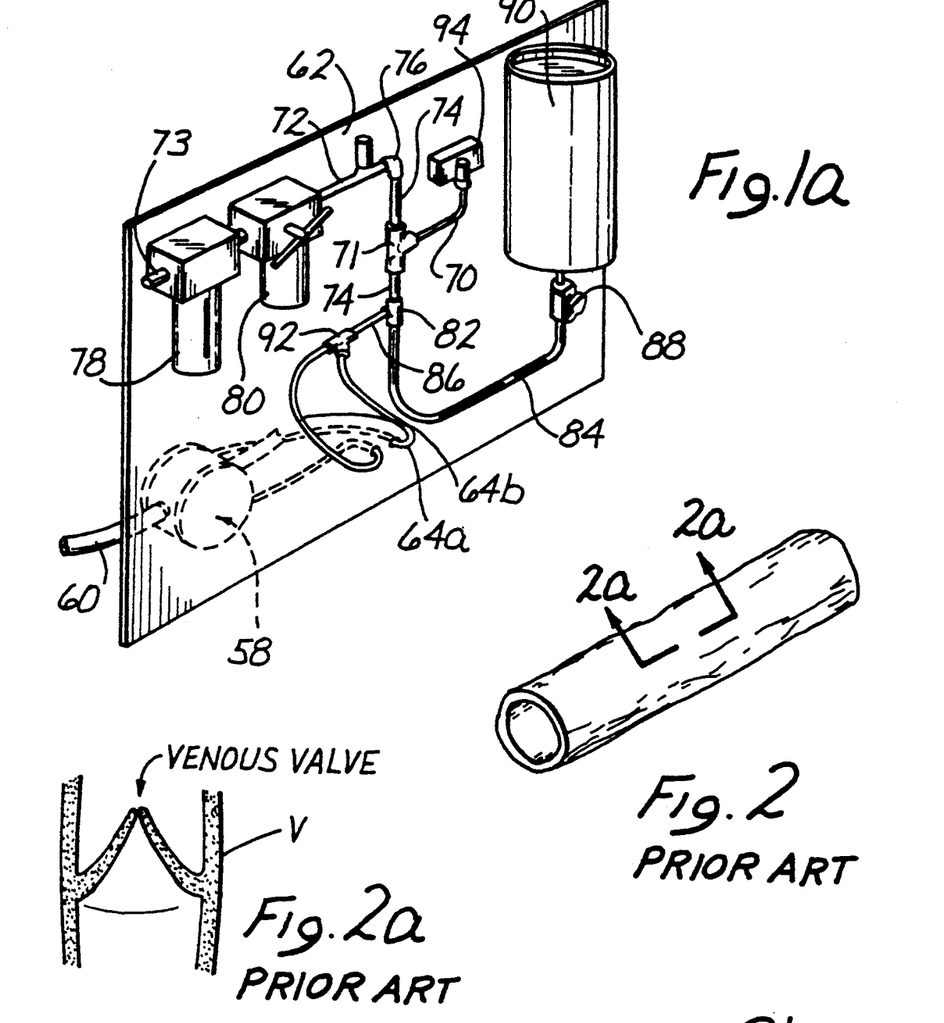
FIG. 1a is a rear perspective view of a portion of the venous valve testing device shown in FIG. 1.
FIG. 2 is a perspective view of a prepared segment of vein having a venous valve located therein.
FIG. 2a is a longitudinal sectional view of a venous valve taken through line 2a—2a of FIG. 2.

The overall configuration and construction of an embodiment of the venous valve function tester (VVFT) of the present invention is shown in FIGS. 1 and 1a. Specific detailed descriptions of individual components of the VVFT are provided herebelow and shown in FIGS. 3–8. Also, a specific description of the preferred method of testing venous valves in accordance with the present invention is set forth hereinbelow and illustrated in Examples 1 and 2.

Prior to considering the specific structural and functional attributes of the preferred individual components of the VVFT, it is expedient to first describe, in general terms, the overall structure and function of this embodiment of the VVFT. In overall configuration, this embodiment of the VVFT comprises a fluid filled recirculating system having (a) a fluid reservoir component 26; (b) a muscle pump component 16; (c) a sample chamber assembly comprising a sample chamber 10, an inlet block 12 and an outlet block 14; (d) a respiratory pump component 50; (e) a capacitance reservoir 58; and (f) a hydrostatic column such as a vertical stand pipe 102 of adjustable height. These individual components (a through f above) are interconnected by flexible and/or rigid tubing so as to provide a recirculating liquid flow system. A sample segment of vein V or tubular prothesis having one or more venous valves positioned therein is mounted in the sample chamber to receive liquid flow which mimics or simulates the hemodynamic and pressure characteristics created in the body through (a) the action of the heart itself in pumping blood through the vascular tree; (b) the "muscle pump" effect created by movements of the visceral organs and somatic muscles; and (c) the "respiratory pump" effect created by the normal cyclic variations in intra-thoracic pressure which occur during respiration due to respiratory movement of the thoracic muscles and diaphragm.

In the embodiment shown, the recirculating system incorporates a fluid reservoir component 26. Such fluid reservoir 26 comprises a container portion 34 having a heavy plastic rectangular base 36 mounted on the bottom thereof with a fluid outlet port 38 formed therein to provide fluid interconnection between the liquid contained within the cylindrical container portion 34 and the fluid supply line 28. An automated temperature control device H, such as a thermostated electric heating element or in line heating coil is positioned in contact with the liquid so as to permit adjustment and control of the temperature of the liquid (e.g. 0.9% saline solution) within the system.

Also, in the embodiment shown, the fluid reservoir component 26 is positioned on a variable height jack apparatus 40 such that the height of the fluid within reservoir component 26 may be varied so as to alter the pressure head or back pressure within the system, as discussed more fully herein.

A fluid outlet tube 44 connects the outlet port 46 of outlet block 14 to the inlet port 48 of a respiratory pump component 50. The respiratory pump 50 comprises an enclosed chamber having an expandable diaphragm positioned therein and connected by respiratory pump air supply tube 52 to a pulsed pressure generator (not shown) so as to cause the diaphragm member 368 positioned within the respiratory pump 50 to undergo repeated expansion and contraction, thereby mimicking the hemodynamic effects of the changes in intra-thoracic pressure which occurs as a result of normal respiratory movements of the thoracic muscles and diaphragm.

The outlet port 54 of the respiratory pump 50 is fluidly connected to the inlet port 56 of capacitance reservoir component 58 by way of tube 60.

The capacitance reservoir component 58 (hereinafter described in more detail) comprises a hollow inner chamber 408 having opposing inner and outer diaphragm members 200, 202, balloons or other inflatable space-occupying members positioned therewithin. The diaphragm members 200, 202 or other space-occupying members are inflatable by air pressure to occupy varying portions of the area within the inner chamber 408 of the capacitance reservoir 58. Thus, by altering the degree of inflation of the inner and outer diaphragm members 200, 202, the operator of the venous valve function tester may bring about desired variations in the available volumetric capacity of the inner chamber so as to provide changes in capacitance of the flow circuit similar to those which occur physiologically in the human vasculature. In the embodiment shown, the capacitance reservoir 58 is mounted on the front of a vertical board 62. Outer 64a and inner 64b air tubes extend through apertures in the board 62 and are fluidly connected to outer and inner sides of the capacitance reservoir 58 so as to provide air pressure for inflation and deflation of the right and left diaphragms positioned within the capacitance reservoir 58, as more fully discussed herebelow.

A compressed air regulating system for operating the capacitance reservoir 58 may be mounted on the backside of board 62, as shown in FIG. 1a.

The compressed air regulating system shown in FIG. 1a comprises a system of tubes, filters, a pressure regulator, a pressure gauge and a damping tank.

Specifically, a first inlet tube 72 is provided with an inlet connector 73 at one end thereof for fluidly connecting such first inlet tube 72 to an adjacent source of compressed gas (e.g. a wall compressed air outlet, a cylinder of compressed nitrogen, etc.). A first filter 78 is positioned on first inlet tube 72 adjacent inlet connector 73 for filtering the air or other compressed gas as it passes into the system. A regulator 80 is also positioned on first tube 72 for permitting regulation and adjustment of the pressure of air or other gas passing into the system.

First inlet tube 72 leads through elbow 76 into secondary vertical line 74. A T-connector 71 positioned in vertical line 74 provides fluid connection of a side tube 70 to the inner bore of vertical tube 74. Side tube 70 is connected to a pressure gauge 94 which is viewable through the front side of board 62. Pressure gauge 94 is fluidly connected to vertical line 74 so as to continually monitor and display the pressure therein.

A second T-connector 82 is mounted at the base of vertical line 74. Damping tank connector line 84 extends from one side of T-connector 82 to damping tank 90. An openable and closable valve 88 is positioned on damping tank connector line 84, near the point at which damping tank connector line 84 enters the base of damping tank 90. The other side of T-connector 82 is connected to line 86 which, by way of yet another T-connector 92 is bifurcated into the outer 64a and inner 64b air tubes which connect to the inner and outer diaphragms of the capacitance reservoir 58.

The damping tank 90 in this preferred embodiment, comprises a cylindrical acrylic tank having a height of approximately 9 inches and a diameter of approximately 4 inches. Such damping tank 90 serves to increase the volume of compressed air or other gas behind diaphragm 200, 202.

By such arrangement, the compressed air regulating system, as shown in FIG. 1a, serves as a means for providing controlled and equivalent pressure to the inner 400 and outer 402 diaphragms of capacitance reservoir 58.

The outlet port 100 of capacitance reservoir 58 leads into a rigid stand pipe 102 formed of material such as rigid plastic tubing and/or flexible plastic tubing held in a generally vertical orientation. Preferably the height of the vertical standpipe 102 is adjustable to permit variability and adjustment of the hydrostatic force against which the recirculating liquid must flow. Such variability or adjustment of the height of standpipe 102 permits the VVFT to be utilized to mimic or simulate various postural positions (i.e. standing versus sitting versus laying) of the human body. Such variability of the standpipe 102 height may be achieved by forming the standpipe of the multiple telescoping sections. Alternatively, the upper portion of the standpipe 102 may be formed of flexible (e.g. Tigon TM) tubing and a variable height support member 103 may be provided to hold and affix various lengths of the upper flexible tube in a vertical orientation, as shown.

The vertical portion of stand pipe 102 is preferably between 10-50 inches in length and, in the embodiment shown, is about 20 inches in length.

A section of flexible tubing (e.g. Tigon TM Tubing, Dow-Corning Corporation, Midland, Mich.) connected at one end to the top end of stand pipe 102 and at the other end to vertical drain tube 106. Vertical drain tube 106 extends into the interior of the fluid reservoir 26, preferably beneath the normal fluid level therein, such that liquid may drain into the reservoir 26 without undue frothing or agitation.

ii. The Sample Chamber Component

Figure 4:
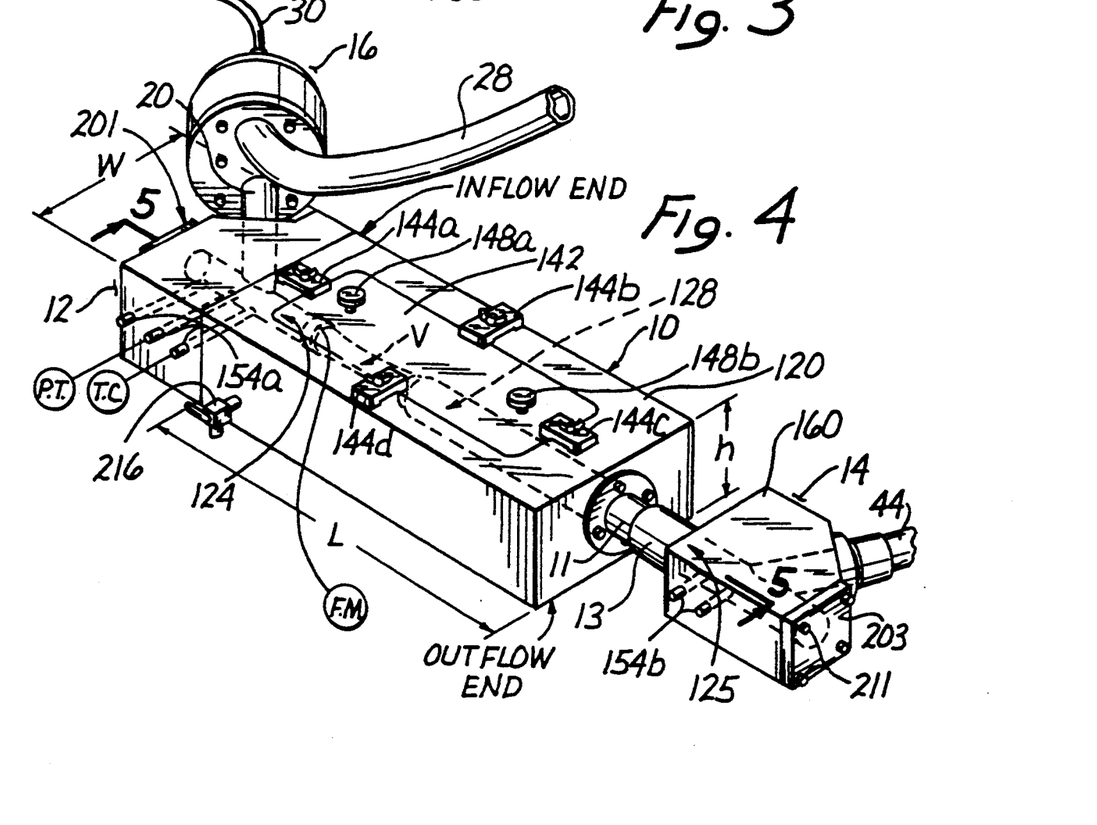
FIG. 4 is a perspective view of a portion of the embodiment shown in FIG. 1, including the (a) muscle pump component, (b) inlet connector block, (c) sample chamber and (d) outlet connector block thereof.
Figure 5:
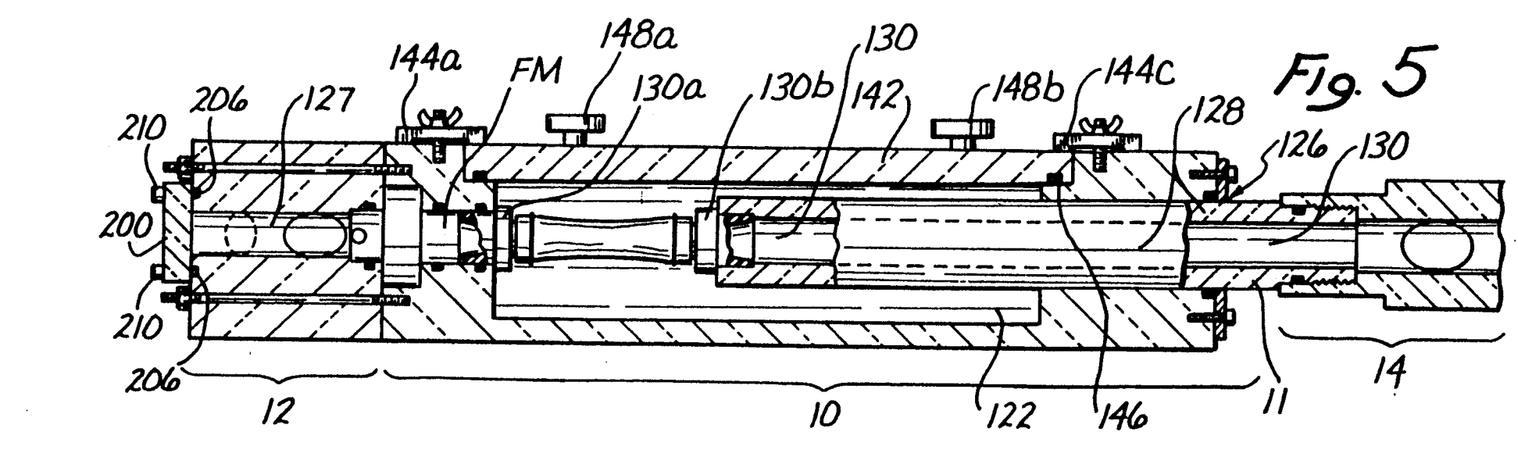
FIG. 5 is a longitudinal sectional view through line 5—5 of FIG. 4.

A specific, preferred embodiment of the sample chamber assembly is shown in FIGS. 4 and 5.

In the embodiment shown, the sample chamber assembly comprises a sample chamber 10, an inlet block 12 and an outlet block 14.

The sample chamber 10 comprises a rigid block 120 of plastic material such as transparent polycarbonate. The block 120 has a length L of approximately 10-20 inches and preferably about 17 inches, a width W of approximately 5-10 inches and preferably about 7 inches and a height H of approximately 3-5 inches and preferably about 4 inches.

A generally rectangular well or depression 122 is formed within the interior of the block 120, forming a rectangular opening in the top surface thereof.

A hollow inlet channel or bore 124 extends through the inflow end of the block 120 into the well or depression 122 so as to provide an inlet fluid flow path through the inflow end of the sample chamber into the well or depression 122 thereof.

A hollow outlet channel or bore 126 extends from the opposite end of the inner well 122 and out of the outflow end of block 120 so as to provide for fluid outflow from the sample chamber component 10. An elongate tubular member 128 extends through the bore 126 and into the interior of well 122, as shown. A portion 11 of such cylindrical tubular member 128 extends beyond the outflow end of block 120 so as to form a fluid conduit for fluid attachment to the attendant outflow block 14, as further described hereinafter.

A sample mounting fixture is formed by a first sample mounting fixture 130a and a second sample mounting fixture 130b. The first sample mounting fixture 130a is partially inserted into and attached to the hollow bore 124 formed in the inflow end of the block 120. The second sample mounting fixture 130b is partially inserted into and attached to the inner lumen 130 of elongate cylindrical tube member 128 as shown. The sample mounting fixtures 130a and 130b are sized and configured and positioned in spaced apart juxtaposition to one another to receive and hold the opposing ends of an artificial or natural venous segment or tubular prostheses having a venous valve positioned therein. The ends of the sample V are attached to the opposing projections of sample mounting fixtures 130a, 130b by tying suture material therearound or otherwise wrapping ligatures therearound to hold the sample V on the projections of the opposing sample mounting fixtures 130a, 130b.

Figure 5A:
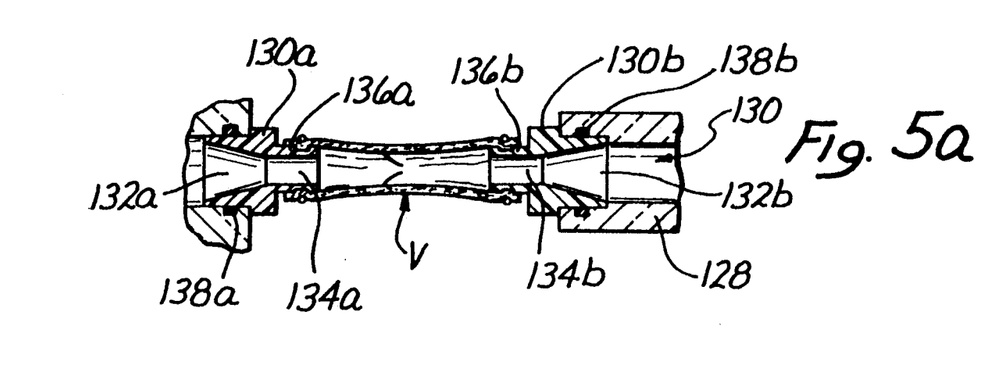
FIG. 5a is a longitudinal sectional view of a preferred sample mounting fixture for mounting a segment of vein within the sample chamber component of the venous valve testing device of the present invention.
Figure 6:
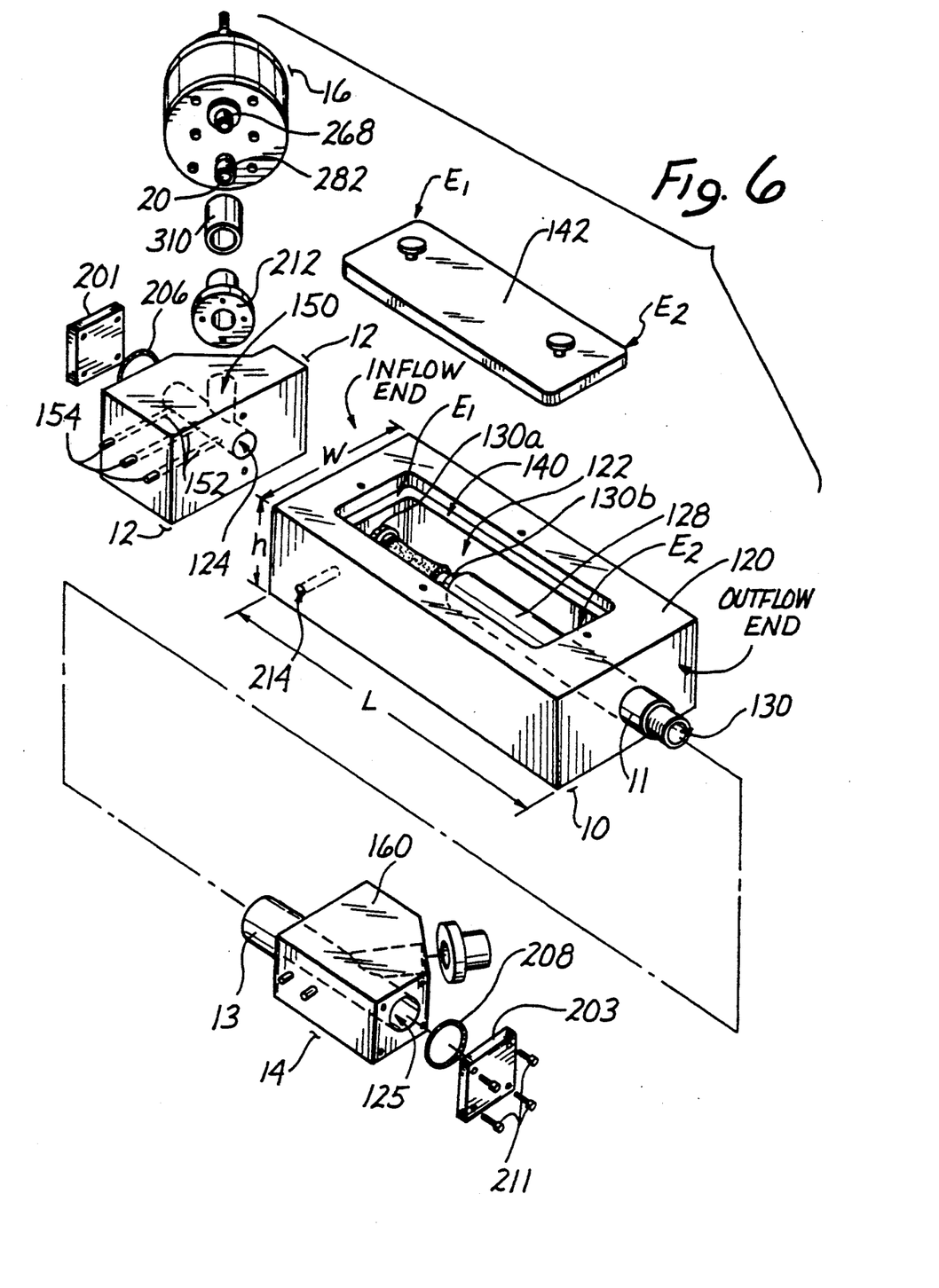
FIG. 6 is an exploded view of the (a) muscle pump component, (b) inlet connector block, (o) sample chamber and (d) outlet connector block portions of a venous valve testing device of the present invention.

As shown in the detailed showing of FIG. 5a, the preferred sample mounting fixtures 130a, 130b comprise generally cylindrical plastic members having frustoconical or tapered outer bore portions 132a, 132b which lead into cylindrical inner bore portions 134a, 134b of generally consistent diameter. A tubular projection 136a, 136b formed on the inside of each sample mounting member 130a, 130b has an outer diameter approximately equal to the inner diameter of the segment of vein V or other specimen to be mounted thereon. Threads, retaining lugs or ridges 138a, 138b are formed in the outer surface of the mounting members 130a, 130b to facilitate holding of such mounting members 130a, 130b in their respective positions within bore 124 and lumen 130. Corresponding notches are formed within the walls of bore 124 and lumen 130 to receive lugs 138a, 138b therein.

The upper opening of well 122 is slightly enlarged so as to form an abutment ridge 140 about the upper perimeter of the well 122. A lid 142 is sized and configured to seat upon abutment ridge 140 and to be affixed thereon by way of clamp members 144a, 144b, 144c, 144d. A rubber seal 146 is formed about the underside of the lid 142 so as to form a fluid tight seal between lid 142 and ridge 140. A pair of handle members 148a, 148b are formed on the upper side of lid 142 to facilitate placement and removal thereof.

The lid 142 is preferably shaped in a manner that will prevent the formation of large air bubbles or voids under the lid when the well 122 is filled with liquid up to the level of abutment ridge 140. Specifically, in the preferred embodiment shown in FIG. 6, the lid 142 is bowed or downwardly convexed or otherwise shaped or sloped such that the lid 142 may be placed on top of liquid within the well 122 without trapping or holding air bubbles under lid 142, as may occur if the underside of the lid 142 were perfectly flat or upwardly concaved.

The inlet block 12 portion of the sample chamber assembly comprises a block of ridged and preferably transparent plastic of generally the same height and width as the sample chamber block member 120. A first inner bore 124 extends longitudinally through the inlet block member 12 as shown. A second hollow bore 150 extends through a sidewall of the block member 12 and into the mid-region of the first bore 124 joining the first bore at an acute angle to permit smooth flow of liquids from the second bore into the first bore.

The size of the lumens 124, 125, 127, 130, 150 are preferably about 24 millimeters in diameter. It is anticipated that the largest venous valve size which would generally be tested with the device is 24 millimeters in diameter. Thus, the bore or lumens 124, 125, 127, 130, 150 of the components of the sample chamber assembly are sized to accommodate valves of 24 millimeter diameter or less without requiring an increase or enlargement in the luminal diameter of the sample mounting chamber and/or sample mounting members 130a, 130b.

The elongate tubular member 128 is slidably disposed within the bore which extends through block 120 such that the tubular member 128 may be slidably moved back and forth to adjust the portion 11 of such tubular member 128 that protrudes beyond the outflow end of the block 120. Such movement of the tubular member 128 enables the distance between sample fixtures 130a, 130b to be adjusted to receive varying lengths of sample V. In the presently preferred embodiment, the tubular member 128 is slidably movable such that the distance between sample mounting fixtures 130a, 130b may be varied from approximately 2 cm to approximately 25 cm in length, thereby enabling the device to receive and hold segments of vein V which range in length from approximately 2 cm to approximately 25 cm.

The sample chamber assembly is also configured and equipped to permit direct visual inspection of the functioning valve within sample V as the device is being operated. To permit such visual inspection, sample viewing windows 201, 203 are mounted at the outward ends of inlet block 12 and outlet block 14 respectively. 0 ring 206 is positioned against the outer surface of inlet block 12 around the open end of bore 124 and window 201 is firmly tightened upon 0 ring 206 by way of bolts or screws (210). Such provides a viewing window for looking directly through bore 124 into the inner lumen of sample V. Similarly, at the opposite end of the sample chamber assembly, 0 ring 208 is positioned against the outer end of outlet block member 14, around the open end of bore 125 and window 203 is firmly tightened upon 0 ring 208 by way of bolts or screws 211 thereby forming a viewing window for looking directly through bore 125 and into the lumen of sample V.

A drain port 214 extends through the wall of the sample chamber block 120 to permit draining of the inner well 122 thereof. A stop cock or valve 216 may be positioned in such drainage port 214 to permit selective draining or venting of liquid from the well 122 of the sample chamber component 10.

A plurality of access ports 154a, 154b or small hollow passageways are formed in inlet block 12 and/or outlet block 14 to permit sampling or direct contacting access to liquid flowing through the sample chamber flow conduit. Various instruments, such as thermocouples and pressure transducers, may be inserted through or fluidly connected to ports 154a, 154b. In the embodiment shown a separate electromagnetic flow meter probe FM is mounted annularly about the sample chamber flow conduit to permit an attached flow meter to continually monitor the flow rate of liquid through the sample chamber flow conduit.

iii. The Muscle Pump Component

Figure 3:
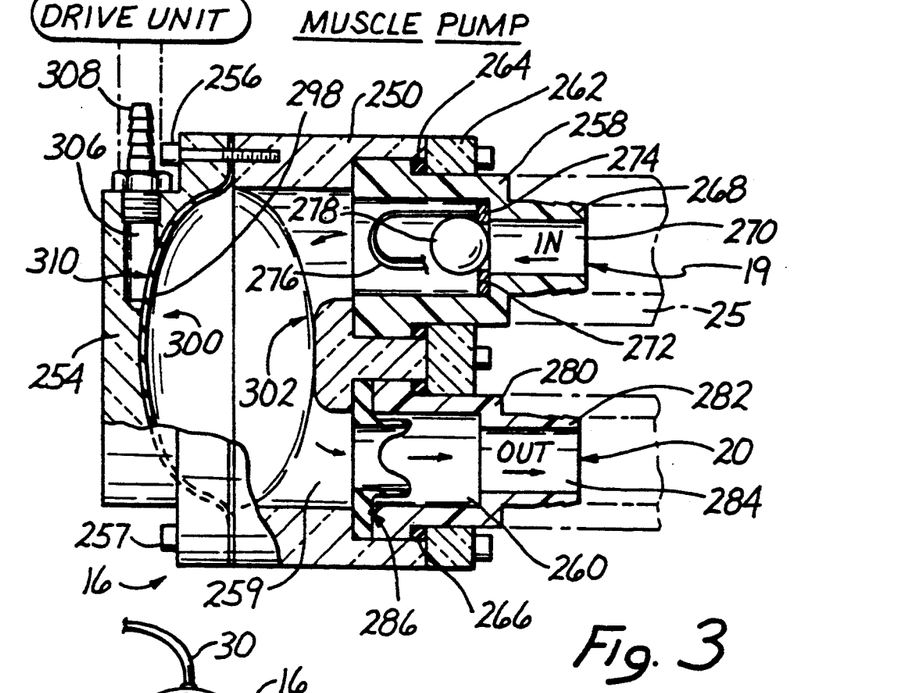
FIG. 3 is a cross sectional view through line 3—3 of the muscle pump component of the device shown in FIG. 1.

An embodiment of the muscle pump 16 is shown in FIG. 3. Such muscle pump 16 comprises a cylindrical plastic shell 250 having a hollow inner chamber 259 formed therein. An end cap member 254 is mounted on one end of the cylindrical plastic shell 250 and is secured in place, as shown, by mounting screws 256, 257. An inlet block member and an outlet block member 260 are mounted within the cylindrical plastic shell 250 and are clamped in place by affixation of rear cap member 262 thereon, so as to compress O-rings 264, 266 and formed fluid tight seals around the inlet 258 and outlet 260 block members.

The inlet block member 258 comprises a generally cylindrical plastic member having a serrated connector projection 268 extending therefrom. Serrated connector projection 268 has a hollow chamber 259 extending therethrough and is sized and configured to receive and hold the end of a flexible tube (e.g. Tigon TM Tubing) thereon. By such arrangement, the fluid supply tube 28 may be attached, in fluid tight connection, to the inlet of muscle pump 16.

Figure 3A:
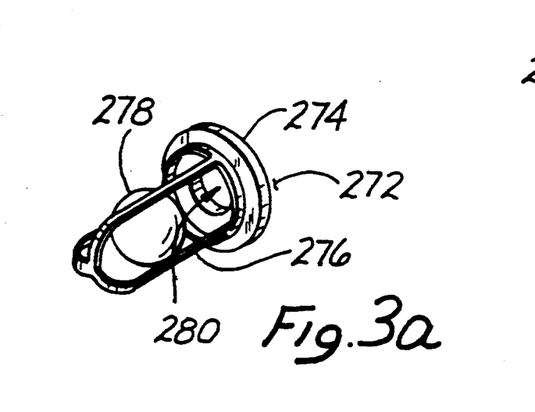
FIG. 3a is a perspective view of the ball-in-cage inflow check valve mounted in the pump assembly of FIG. 3.

An inlet check valve 272 is positioned within the inner bore of inlet block member 258 so as to allow inward flow of fluid into the muscle pump 16 but to substantially prevent and deter outward backflow of fluid out of the inner bore 270 of projection 268. One type of inlet check valve 272 usable in the muscle pump 16 is shown in FIG. 3a. As shown, this preferred inlet check valve 272 comprises a ball-in-cage type valve comprising an annular seat member 274, a rigid cage 276 and a ball 278 positioned within cage 276 so as to be movable between a closed position wherein the ball 278 is seated against the annular base 274 so as to close off aperture 280 and an "open" position wherein the ball 278 is moved away from the annular base member 274 so as to allow fluid flow through in the inward direction (see arrow on FIG. 3) through the aperture 280 in the annular base member 274 of the inlet valve 272. The ball-in-cage type inlet check valve of this embodiment is commercially available as the Star-Edwards Silastic TM aortic ball valve.

The outlet block member 260 also comprises a plastic cylindrical body 280 having a tubular projection 282 extending outwardly therefrom. Serrated tubular projection 282 has a hollow cylindrical inner bore 284 which forms the outlet port 20 of muscle pump 16.

Figure 3B:
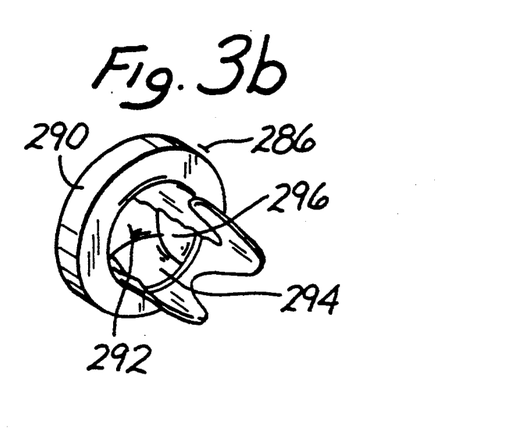
FIG. 3b is a cut away perspective view of the tricuspid outflow check valve mounted in the pump assembly of FIG. 3.

An outlet check valve 286 is mounted within the outlet block member 260 so as to permit outflow of liquid through the outlet port 20 of muscle pump 16 while preventing inward regurgitation or backflow of such fluid into the inner chamber 252 of the muscle pump 16. The outlet valve 286 may comprise any suitable type of valve capable of carrying out the desired check valve function. A preferred embodiment of the outflow check valve 260 is shown in FIG. 3b. Such preferred outflow check valve 260 comprises a tricuspid leaflet-type check valve having an annular base portion 290 with three flexible leaflets 292, 294, 296 projecting therefrom, as shown. Such flexible leaflets are sized and configured to bend inwardly and to contact one another, thereby forming a substantially fluid tight closure upon exertion of backflow pressure thereon but to prevent unrestricted movement of fluid in the outward direction (see arrows on FIG. 3) therethrough.

The preferred muscle pump component 16 is a diaphragm-type pump. In the embodiment shown, a flexible diaphragm member 298 is positioned within the inner chamber 259 of the pump 16 with the outer perimeter of the flexible diaphragm 298 being captured and held between the opposing surfaces of cylindrical shell 250 and outer cap member 254. Apertures are formed in the perimeter of the flexible diaphragm 298 to allow passage of bolts 256, 257 therethrough.

Opposing semi-ovoid cavities 300, 302 are formed within the inner chamber 259 of the muscle pump 16. Resilient diaphragm member 298 is mounted midway between such opposing semi-ovoid cavities 300, 302 as shown. Such resilient diaphragm member 298 is mounted and held in place by compression of the periphery of the diaphragm member 298 between the surfaces of the cylindrical muscle pump body 250 and the outer cap member 254, as shown. A hollow fluid inlet/outlet passageway 306 extends through a portion of the outlet cap member 254 and a tubing connector 308 is positioned thereon. A pneumatic pulse drive device, capable of providing timed pulsatile positive pressure or positive and negative pressure outputs for the purpose of causing the desired repetitive movement of diaphragm member 298. Examples of a commercially available pneumatic pulse drive units usable to drive the muscle pump 16 (and/or respiratory pump 50) include that manufactured by Totten Scientific, 4040 Leisure Lane, Placerville, Calif. 95667 and the "Philadrive 2" available from Cardiac Systems, Inc. Conshohecken, Pa. 19428.

In normal operation, the flexible liquid supply line 28 is connected to inlet tubing connector projection 268 and one end of outlet tube 310 is connected to the outlet tubing connector projection 282. The opposite end of outlet tube 310 is fluidly connected to the inlet port 22 or inlet opening of inlet block member 12 of the sample chamber assembly by way of rigid attachment member. A liquid such as saline solution is placed within fluid reservoir 26 and is allowed to fill fluid supply line 28. The pneumatic pulse drive unit is attached to tubing connector 308 and is actuated so as to provide pulsatile pressure Within passageway 306 against the backside 310 of diaphragm 298. Preferably, such pulsatile pressure will repeatedly cycle from a period of positive pressure to a period of reduced positive pressure/ambient pressure or negative pressure (vacuum), the subsequently back to the original level of high/low, positive pressure, etc... Such alternating positive/negative or positive/ambient pressure provided by the pulse drive unit will cause the diaphragm 298 to move back and forth in a manner that results in the desired pumping of liquid through pump 16. To wit: when the pressure exerted on the behind diaphragm 298 is less than the pressure being exerted against the front of diaphragm 298, such will cause diaphragm 298 to move outwardly and into abutment against the outer semi-ovoid surface 300. Thereafter, when positive pressure is applied behind diaphragm 298 and such positive pressure exceeds the pressure being exerted against the front of diaphragm 298, such will cause diaphragm 298 to involute or move inwardly to a position where diaphragm 298 abuts against inner semi-ovoid surface 302. The amount of pressure being exerted against the front of diaphragm 298 may be varied by adjusting the height of jack 40 under fluid reservoir 26.

The above-described cyclic back and forth movement of diaphragm 298 serves to operate muscle pump 16 as follows:

1. Movement of the diaphragm from the "second" position (in abutment against inner semi-ovoid surface 302) to the "first" position (in abutment against outer semi-ovoid surface 300) will cause fluid to be drawn or pulled into the inner chamber 259 of muscle pump 16 through the hollow bores 270, 272 or inlet block member 258, causing inlet check valve 272 to open, and outlet check valve 286 to close.

2. Movement of the diaphragm from the "first" position to the "second" position will expel liquid out of the outlet port 20 of muscle pump 16. In so doing, the positive pressure exerted by movement of the diaphragm 298 will cause the closure of inlet check valve 272 and opening of outlet check valve 286. The liquid contained within the inner chamber 259 of the pump 16 will thus be expelled outwardly through the inner bores 260, 284 of the outlet block 280 and through the outlet tube 310. Outlet tube 310 is fluidly connected to the inlet port 22 at the open end of bore 150 by way of rigid connector member 212. Thus, liquid pumped out of muscle pump 16 will flow through the sample chamber assembly and through the sample segment of vein (V), as shown.

The pulsatile rate and positive/negative pressure(s) provided by the pressure pulse drive machine may be varied to approximate and simulate variations in normal or abnormal peripheral muscle activity.

Although the functioning of the muscle pump 16 has been specifically described above with respect to relative pressure changes being effected on the front versus back of diaphragm 298 pressure provided by the attendant pressure pulse drive machine, it will be appreciated that, in embodiments where the muscle pump diaphragm member 298 is sufficiently elastic or resilient and biased to automatically return to said "first" position whereby said diaphragm member 298 is in abutment with the outer semi-ovoid wall 300, the attendant pressure pulse drive machine may be adapted to vary between (a) ambient pressure and (b) positive pressure such that during the period when the pressure pulse drive machine is emitting only ambient pressure, the resiliency and bias of the diaphragm member 298 will cause it to automatically return to said its "first" position against outer semi-ovoid wall 300.

iv. Respiratory Pump Component

Figure 7:
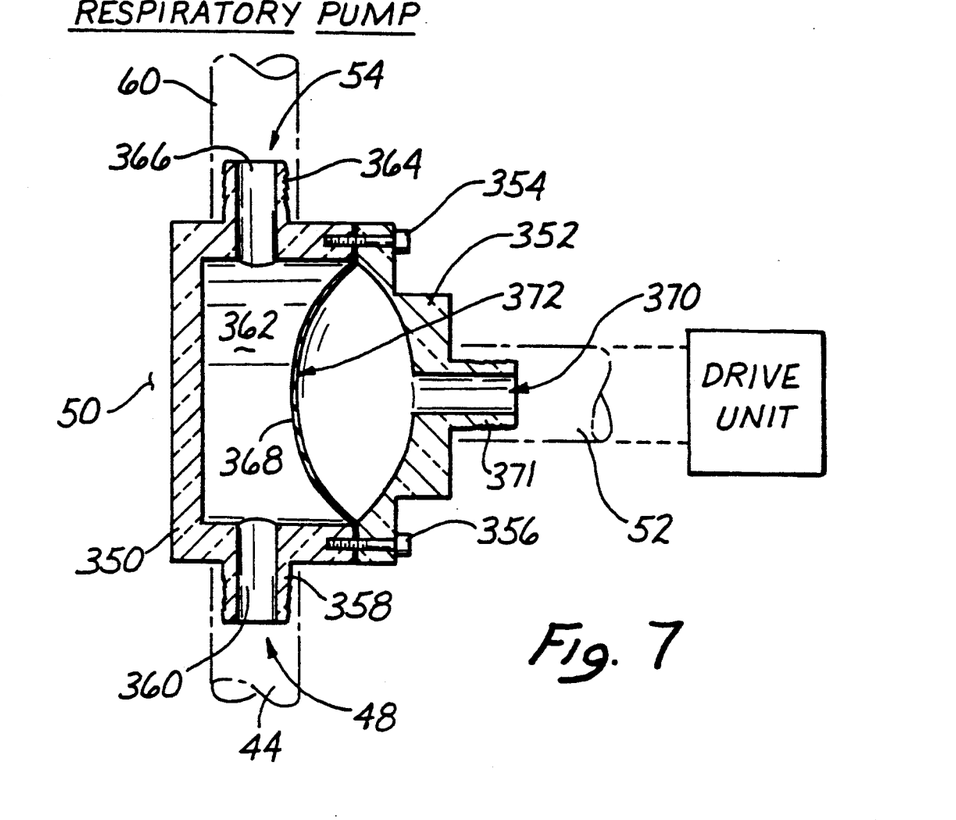
FIG. 7 is a cross-sectional view through line 7—7 of FIG. 1.

A presently preferred embodiment of the respiratory pump component 50 is shown in FIG. 7. As shown, this embodiment of the respiratory pump 50 is a simple single diaphragm chamber comprising a rigid plastic chamber body 350, having a cover member 352 mounted thereon by bolts or screws 354, 356. The inlet 40 of respiratory pump 50 comprises a serrated tube mounting projection 358 having a hollow inner bore 360 extending therethrough to provide a fluid passageway into the hollow inner chamber 362 of the pump 50. The outlet port 54 of pump 50 comprises a serrated outlet tubing mount projection 364, also having a hollow inner bore 366 extending therethrough so as to provide a fluid passageway from the inner chamber 362 of muscle pump 50 into the attached outflow tube 60. A resilient diaphragm 368 is mounted within chamber 362 by compressing the periphery of the diaphragm between the body of the chamber 350 and the periphery of the lid member 352. One or more rigid washers or gaskets may be positioned on either side of the diaphragm periphery to facilitate fluid tight sealing of the components. Apertures are formed in the periphery of the diaphragm to allow passage of screws 354, 356 therethrough.

A pulsed pressure inlet 370 comprises a hollow bore or passageway which extends through the cover member 352 to permit passage of pulsed positive/negative or positive/ambient pressure therethrough. Such pulsed pressure will be exerted against the back side 372 of diaphragm 368. A tube mounting projection 371 is formed on the outer side of cover member 352 to permit fluid connection of a pulse pressure supply tube 52 which provides the flow of pulsed air or gas pressure from the attendant pulsed pressure drive machine shown. The pulse frequency and amount of positive and/or negative pressure generated by the drive unit may be adjusted to approximate or simulate the intravascular effect of normal or abnormal variations in intra-thoracic pressure that occur during normal respiration.

The diaphragm 368 is thus made to travel between its inflated position (shown in FIG. 7) and a deflated position in which the diaphragm 368 is withdrawn and pulled against the concave inner surface of lid member 352.

v. Capacitance Reservoir Component

Figure 8:
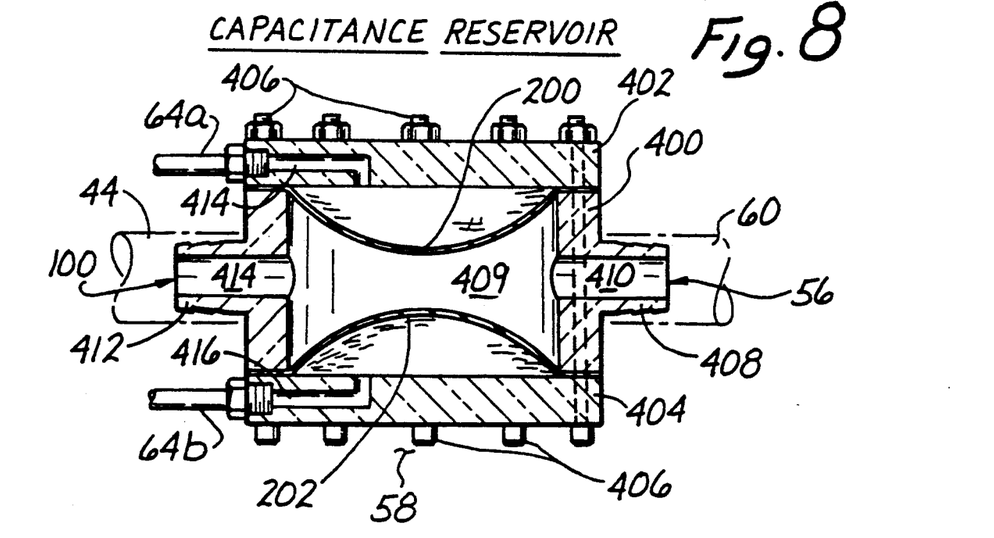
FIG. 8 is a cross-sectional view through line 8—8 of FIG. 1.

A preferred embodiment of the capacitance reservoir component 58 is shown in FIG. 8.

As shown, such preferred capacitance reservoir component 58 comprises a rigid outer shell having a hollow inner chamber 408 formed therein. The rigid outer shell comprises a cylindrical shell member 400 and inner and outer cap members 402, 404. The cap members 402, 404 are connected to the cylindrical member 400 by way of bolts 406 so as to form a fluid tight chamber therein.

The inlet port 56 of the capacitance reservoir 58 comprises a tubular projection 408 having a serrated outer surface for receiving and frictionally engaging flexible tube 60 thereon. A hollow bore 410 extends through tubular projection 408 to provide fluid communication between the lumen of tube 60 and the inner chamber 408 of the capacitance reservoir 58.

The outlet port 100 of capacitance reservoir 58 comprises a tubular projection 412 having a serrated outer surface for receiving and frictionally holding tube 44 thereon. A hollow inner bore 414 extends through the tubular projection 412 to permit fluid to flow from the inner chamber 408, outwardly, through the lumen of tube 44.

Resilient diaphragm members 200, 202 are positioned on the inner and outer sides of the inner chamber 408. Each such diaphragm member is held firmly in place by compressing the periphery of the diaphragm between the outer edges of the cylindrical body 400 and the respective inner 402 or outer 404 cap member. Apertures are formed about the periphery of each diaphragm member 200, 202 to permit the passage of bolts 406 therethrough.

Air supply passageways 414, 416 are formed in the inner 402 and outer 404 cap members as shown. Inner air supply tube 64a is fluidly connected to the inner air passageway 414 to provide a flow of compressed air into the space between inner diaphragm member 200 and the inner surface of inner cap member 402. Likewise, outer air supply tube 64b is fluidly connected to outer air supply passageway 416 so as to provide a flow of compressed air into the space between the inner surface of outer cap member 404 and outer diaphragm member 202.

The preferred capacitance reservoir 58 shown in FIG. 8 operates by alteration of the air pressure provided behind diaphragms 200 and 202, thereby altering the size and volumetric capacity of inner chamber 408. In operation within the system shown in FIG. 1a, such alteration in pressure is effected by setting regulator 80 to a desired air pressure level. Upon such setting of regulator 80, equivalent air pressure will be provided through inner 64a and outer 64b air supply tubes and will cause equivalent bulging or inflation of resilient diaphragms 200 and 202, thereby bringing about a desired degree of constriction within inner chamber 408. When the air pressure provided through tubes 64a, 64b is lessened, the resilient diaphragm members 200, 202 will retract, thereby enlarging the volumetric capacity of chamber 408. Similarly, when the air pressure provided through tubes 64a, 64b is increased, the resilient diaphragm members 200, 202 will become more expanded and will move closer to one another, thereby decreasing the volumetric capacity of inner chamber 408. By such arrangement, the capacitance reservoir 58 may be operated to vary the degree of capacitance provided to fluid flowing through the venous valve testing system.

In the embodiment shown, the inner chamber 408 of the capacitance reservoir 58 is about 3 inches in width and about 4 inches in length. The diaphragm members 200, 202 are about 4 inches in diameter and may be inflated to a point where they nearly meet and touch one another at their center points. When fully deflated, the diaphragm members 200, 202 are preferably flat against the inner surface of cap members 402, 404.

vi. Preferred Mode of Operation

In a preferred mode of operation, the reservoir component 26 is initially filled with 0.9% aqueous NaCl solution (normal saline) and heater H is energized to warm the liquid to approximately 37° C.

A segment of vein V or tubular prostheses having a venous valve positioned therein is then mounted on the sample mounting fixture by affixing opposing ends of the vein V or tubular prostheses to the opposing sample mounting members 130a, 130b, as shown in FIG. 5a.

After the sample V has been mounted within the sample chamber, the sample chamber well 122 is filled with bath liquid such as 0.9% aqueous NaCl solution. Such bath liquid fully surrounds and immerses the segment of vein V or tubular prostheses. A temperature control element (not shown) may be mounted within the well 122 so as to control the temperature of the bath solution, preferably at approximately 37° C.

The muscle pump component 16 and/or respiratory pump component 50 and/or capacitance reservoir 58 and/or hydrostatic column 102 are then independently operated and adjusted to mimic or simulate a specific intravascular pressure waveform of the type known to occur under specific test conditions.

The following examples serve to illustrate two (2) specific types of test conditions, and specific types of specific waveforms which may be mimicked by the VVFT device:

EXAMPLE 1

The purpose of this experiment is to test the venous valve sample V under conditions which mimic or simulate the actual hemodynamic conditions encountered by a venous valve positioned in the upper femoral vein of the leg of a 35-year old adult human being who is performing a walking or running exercise while in an upright standing posture.

Figure 9:
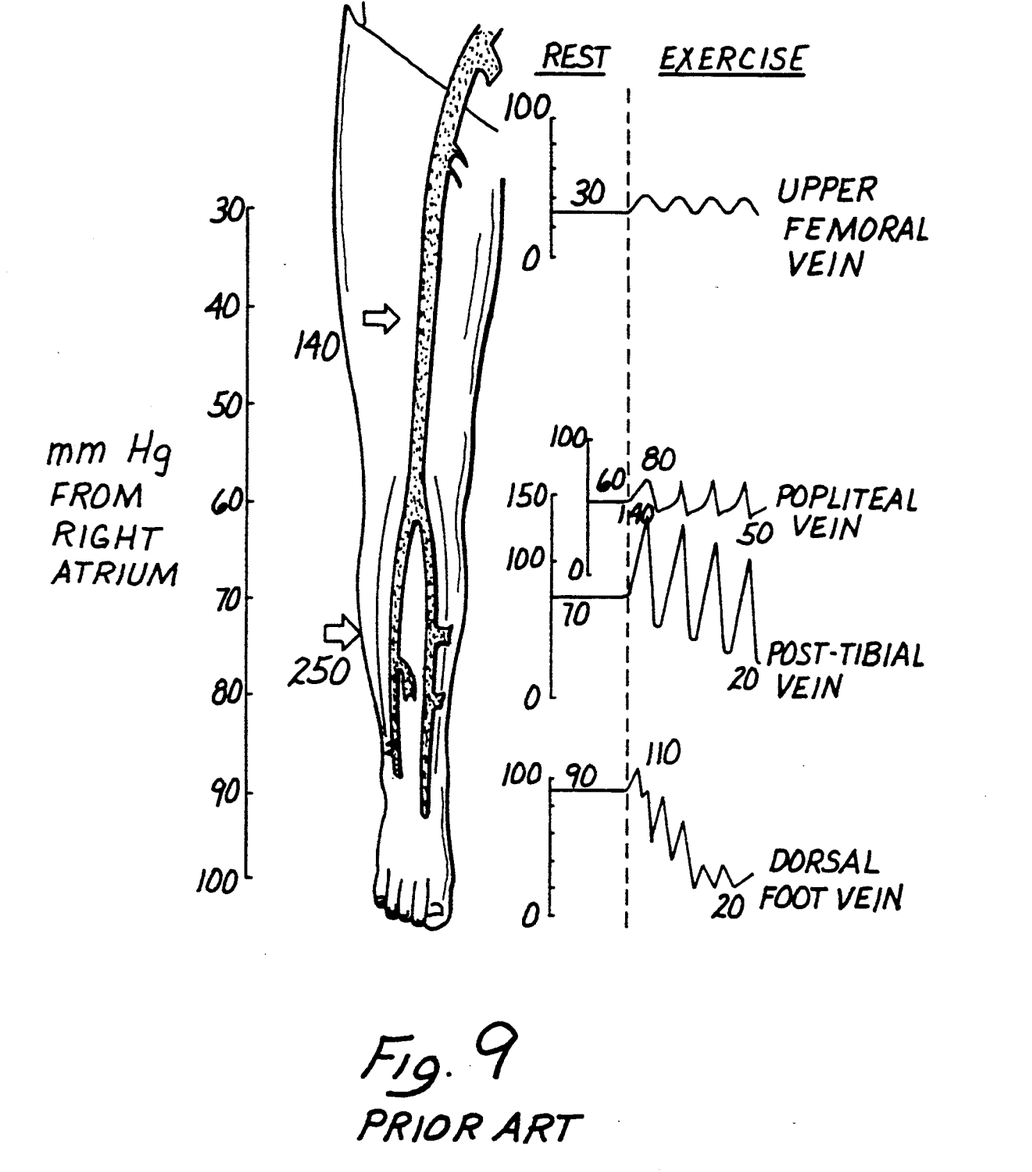
FIG. 9 is a published illustration of the major veins of the human leg with accompanying examples of standard pressure waveforms, under both rest and exercise, at various locations within the illustrated leg veins.

A known hemodynamic waveform for the upper femoral vein of a 35-year old adult, under the above enumerated postural and exercise circumstances is obtained from the literature or generated experimentally by known methodology. An example of such a waveform is shown in FIG. 9. This exemplary waveform was obtained from a published book entitled, "Surgery of The Veins" by Bergan, J. and Yao, J. (1985).

First, the rate (cycles per minute) and outlet peak pressure (mm. Hg) of the muscle pump is set to simulate the muscle pump activity generated by the walking or running movement of the human subject. The pressure within inlet conduit 124 is monitored by pressure transducer PT. Any and all of the individual components (e.g. muscle pump 16, respiratory pump 50, capacitance reservoir 58, and/or vertical hydrostatic tube or column 102) capable of adjustment or variation may be adjusted or varied to arrive at a waveform measured by pressure transducer which is substantially the same as the desired standard waveform obtained from the literature or other known source (i.e. that shown in FIG. 9).

To wit, the rate and peak output force of muscle pump 16 may be adjusted to mimic the rate and force of the muscle pump effect occurring in the leg vein during exercise.

Also, the degree of inflation of the diaphragms 200, 202 within capacitance reservoir 58 may be altered and adjusted to provide a degree of capacitance within the flow path to mimic the venous capacitance which contributed to the target waveform. (FIG. 9)

Also, the height of vertical tube 102 may be altered or adjusted to provide hydrostatic impedance simulative of actual hydrostatic force which contributed to the desired target waveform. Such hydrostatic impedance will in this example be relatively high due to the erect posture of the test subject.

Also, respiratory pump 50 may be energized and adjusted so that the frequency (cycles per minute) and pressure (size and extent of diaphragm protrusion into chamber) of the diaphragm member 368 within respiratory pump 50 serves to mimic or simulate the respiratory pump effect which contributed to the desired target waveform. Since the human is in an exercising state, the frequency and force (depth) of movement of the respiratory pump diaphragm member will likely be relatively high. (e.g. 20 cycles per minute with the diaphragm 368, when fully extended, occupying approximately one third of the total volume of the respiratory pump inner chamber 362).

After any or all of the muscle pump 16 and/or respiratory pump 50 and/or capacitance reservoir 58 and/or hydrostatic column 102 have been individually energized and adjusted, the pressure waveform monitored by pressure transducer PT (and/or other variables such as flow rate waveform monitored by flow meter FM) will be identical or closely simulative of the desired waveform of FIG. 9.

The function of the venous valve during this test may be monitored by visual observation through viewing windows 201, 203 and/or by concomitant monitoring of the consistency of and/or variables such as flow rate and changes in pressure at one or more points within the fluid flow path.

After the test flow cycle has been maintained for a desired period of time, (e.g 1 hour), the test is terminated. The sample segment V is then removed from the sample mounting fixture and the subject venous valve may then be excised and/or removed from sample segment V to permit the value to be examined grossly and/or microscopically to further assess the performance and degree of gross or microscopic changes which have occurred during the test.

EXAMPLE 2

The purpose of this experiment is to mimic or simulate the hemodynamic conditions encountered by a venous valve located in the popliteal vein of the leg of an 80-year old human who remains resting in a dorsally recumbent position, without significant muscular movement of the extremities.

As in the first example (above) a known hemodynamic waveform for an 85 year old human in a dorsally recumbent position without significant muscular movement of the extremities is obtained from the literature or generated experimentally by known methodology.

Since the subject individual is resting without significant muscular movement of the extremities, the muscle pump 16 may be non-functional throughout this experiment, or may be set at an extremely low rate (cycles per minute) and low outlet peak pressure (MMHG) so as to mimic only occasional leg muscle contractions as would likely occur in a dorsally recumbent, bedfast individual.

Also, the degree of inflation of the diaphragms 200, 202 within capacitance reservoir 58 may be altered and adjusted to provide a degree of capacitance within the flow path which is simulative of the venous capacitance which contributes to the target waveform of the test subject.

Also, the height of the vertical column 102 may be altered or adjusted to provide hydrostatic impedance which is simulative of the actual hydrostatic force which contributed to the desired target waveform. Such hydrostatic impedance will, in this example, be relatively low due to the dorsally recumbent posture of the test subject.

Also, respiratory pump 50 may be energized and adjusted so that the frequency (cycles per minute) and pressure (size and extent of diaphragm protrusion into chamber) of the diaphragm member 368 within respiratory pump 50 serves to mimic or simulate the respiratory pump effect which contributed to the desired target waveform. Since the human, in this example, is in a resting state, the frequency and force (depth) of movement of the respiratory pump diaphragm member will likely be relatively low. (e.g. 10 cycles per minute with the diaphragm 368, when fully extended, occupying about ¼ of the total volume of the respiratory pump inner chamber).

After any or all of the muscle pump 16 and/or respiratory pump 15 and/or capacitance reservoir 58 and/or hydrostatic column 102 have been individually energized and adjusted, the pressure waveform monitored by pressure traducer PT (and/or other variables such as flow rate waveform monitored by flow meter FM) will be identical or closely simulative to the desired target waveform.

The function of the venous valve during this test may be monitored by visual observation through viewing windows 201, 203 and/or by concomitant monitoring of the consistency of an/or changes in variables such as flow rate and pressure at one or more points within the fluid flow path.

After the test flow cycle has been maintained for a desired period of time (e.g. one hour) the test is terminated. The sample segment V is then removed from the sample mounting fixture and the subject venous valve may then be excised and/or removed from sample segment V to permit the valve to be examined grossly and or microscopically to further assess the performance and degree of gross or microscopic changes which have occurred during the test.

The invention has been described herein with reference to one specific embodiment of the VVFT and specific examples of test methodology which may be conducted in accordance with the invention. It is intended that the scope of the invention be limited to the specific embodiments described, or the specific examples enumerated, but rather, that the scope of the present invention be construed as encompassing that which is claimed in the following claims and all equivalents thereof.

What is claimed is:

1. A device for testing venous valves, said device comprising:
   (a) a holding fixture for holding a venous valve sample in a substantially fixed position;
   (b) an inflow conduit fluidly connectable to said venous valve for passing a flow of liquid through said venous valve;
   (c) an outflow conduit fluidly connectable to said venous valve to carry liquid which has passed through said venous valve away from said venous valve;
   (d) a muscle pump fluidly connected to said inflow conduit and operative to pump a substantially pulsatile flow of liquid through said inflow conduit and through said venous valve;
   (e) a respiratory pump fluidly connected to said outflow conduit and operative to exert cyclic variations in pressure on liquid exiting said venous valve through said outflow conduit.

2. The device of claim 1 further comprising:
   a fluidic connection between said outflow conduit and said inflow conduit such that liquid flowing through said outflow conduit will recirculate through said inflow conduit.

3. The device of claim 2 wherein said variable capacitance reservoir comprises:
   (i) a rigid outer shell defining an inner chamber therewithin;
   (ii) an apparatus for varying the volumetric capacity of said inner chamber;
   (iii) an inlet port connectable to said outflow conduit to allow liquid from said outflow conduit to pass into said inner chamber; and
   (iv) an outlet port for allowing liquid to flow out of said inner chamber.

4. The device of claim 3 wherein said apparatus for varying the volumetric capacity of the inner chamber of said capacitance reservoir comprises:
   an inflatable space occupying member sized, configured and positioned in relation to said inner chamber such that:
   (a) inflation of the space occupying member will increase the extent to which said space occupying member protrudes into said inner chamber thereby decreasing the available liquid-holding volumetric capacity of the inner chamber and,
   (b) deflation of the space occupying member decreases the extent to which said space occupying member protrudes into the inner chamber thereby increasing the available liquid-holding volumetric capacity of said inner chamber.

5. The device of claim 1 further comprising:
   (f) a variable capacitance reservoir fluidly connected to said outflow conduit, said variable capacitance reservoir comprising a reservoir of variable volumetric capacity.

6. The device of claim 1 further comprising:
   (g) a hydrostatic column fluidly connected to said outflow conduit.

7. The device of claim 6 wherein said hydrostatic column comprises a tubular conduit of variable height to permit variation in the hydrostatic impedance of fluid flowing through the outlet portion of said conduit.

8. The device of claim 1 wherein said holding fixture comprises first and second annular mounting members positioned in opposing juxtaposition to receive thereon and hold the opposite ends of a segment of blood vessel wherein a venous valve is located.

9. The device of claim 1 wherein said muscle pump comprises:
   a rigid outer shell;
   a hollow inner chamber within said rigid outer shell;
   an inlet port connected to a liquid source for passage of liquid into said hollow inner chamber;
   an inlet port check valve positioned in operative relation to said inlet port to permit inflow of liquid into said inner chamber through said inlet port but to substantially prevent backflow of liquid out of inner chamber through said inlet port;
   an outlet port connected to said inflow conduit for passage of liquid out of said inner chamber and into said inflow conduit;
   an outflow check valve positioned in operative relation to said outflow port to permit outflow of liquid from said inner chamber through said outflow port but to substantially prevent inward backflow of liquid into said inner chamber through said outlet port;
   a diaphragm member positioned within said inner chamber and movable back and forth between a "first" position and a "second" position such that:
   (a) as the diaphragm member moves from said "first" position to said "second" position liquid within the inner chamber will be forced outwardly through said outlet port; and
   (b) as the diaphragm member moves from said "second" position to said "first" liquid will be drawn inwardly through said inlet port into said inner chamber; and
   a drive apparatus operatively connected to said muscle pump, said drive apparatus being operative to drive said diaphragm member back and forth between said "first" and said "second" positions.

10. The device of claim 9 wherein said inlet check valve comprises a ball-in-cage valve.

11. The device of claim 10 wherein said inlet check valve comprises a ball-in-cage aortic valve.

12. The device of claim 9 wherein said outlet check valve comprises a tricuspid leaflet-type valve.

13. The device of claim 9 wherein said drive apparatus comprises a pneumatic pulse drive unit.

14. The device of claim 1 wherein said respiratory pump comprises:
    a rigid outer shell;

a hollow inner chamber within said shell;

an inlet port connectable to said outflow conduit such that liquid may flow from said outlet conduit into said inner chamber;

an outlet port for allowing liquid to flow out of said inner chamber;

a diaphragm member positioned within said inner chamber and capable of undergoing repeated inflation and deflation such that:
  (a) inflation of said diaphragm member causes said diaphragm member to protrude into said inner chamber and,
  (b) deflation of said diaphragm member causes said diaphragm member into retract from said inner chamber; and a drive apparatus for alternately inflating and deflating said diaphragm member to thereby exert cyclic variations in pressure on liquid passing through said inner chamber.

15. The device of claim 1 further comprising:
a temperature control device for controlling the temperature of liquid flowing through the device.

16. The device of claim 1 further comprising:
at least one pressure transducer to measure the pressure of liquid flowing through said device.

17. The device of claim 1 further comprising:
a sample chamber having a liquid-holding sample well formed therein, said venous valve holding fixture being located within said liquid-holding sample well such that liquid within said liquid-holding sample well may surround said venous valve sample.

18. The device of claim 1 further comprising:
a viewing window positioned in said device such that a human operator may view the functional movement of the venous valve sample being tested by said device.

19. The device of claim 1 further comprising:
a vertically inclined conduit fluidly connected to said outflow conduit to provide a hydrostatic column against liquid flowing through said outflow conduit.

20. The device of claim 19 wherein said vertically inclined conduit is of adjustable height, to permit adjustment of the amount of hydrostatic impedance created thereby.

* * * * *